United States Patent [19]

Matsumura

[11] Patent Number: 4,659,809
[45] Date of Patent: Apr. 21, 1987

[54] PROCESS FOR PRODUCTION OF SUGAR KETALS

[75] Inventor: Koichi Matsumura, Osaka, Japan

[73] Assignee: Takeda Chemical Industries, Ltd., Osaka, Japan

[21] Appl. No.: 654,249

[22] Filed: Sep. 25, 1984

[30] Foreign Application Priority Data

Sep. 27, 1983 [JP] Japan .................. 58-179872

[51] Int. Cl.[4] .............................. C07H 1/00
[52] U.S. Cl. .................... 536/18.5; 536/4.1; 536/120; 536/124
[58] Field of Search ............ 536/18.5, 120, 124

[56] References Cited

U.S. PATENT DOCUMENTS

| | | | |
|---|---|---|---|
| 3,139,443 | 6/1964 | Sosnovsky | 536/124 |
| 3,598,804 | 8/1971 | Hindley et al. | 536/124 |
| 3,607,862 | 9/1971 | Jaffe et al. | 536/124 |
| 3,622,506 | 11/1971 | Hindley et al. | 536/124 |
| 4,460,767 | 7/1984 | Matsumura et al. | 536/124 |
| 4,464,530 | 8/1984 | Matsumura et al. | 536/124 |

FOREIGN PATENT DOCUMENTS 0076118 9/1982 European Pat. Off. ............ 536/124

OTHER PUBLICATIONS

Journal of American Chemical Society, vol. XLIV, Jul.-Dec. 1922, "A Study of Catalysis in the Preparation of Acetal", by Homer Adkins and Brynjulv H. Nissen.
Organic Synthesis, vol. 1, "Open-Chain Saturated Compounds" by Migrdichian.
Houben-Weyl, vol. 3, p. 215, 1965.

*Primary Examiner*—Johnnie R. Brown
*Attorney, Agent, or Firm*—Wegner & Bretschneider

[57] ABSTRACT

A process is disclosed for production of a sugar ketal, which comprises reacting a sugar with a ketone in the presence of antimony pentachloride or antimony pentafluoride. The process offers characteristic features that the reaction can be allowed to proceed fully in a small amount of the catalyst, the objective sugar ketal being obtained in improved yields.

8 Claims, No Drawings

PROCESS FOR PRODUCTION OF SUGAR KETALS

This invention relates to a process for producing sugar ketals. In more particular, the present invention provides a novel process for producing sugar ketals which are valuable derivatives in the chemistry of sugars.

Sugar ketals, which are not only of considerable importance for the protection of hydroxyl groups and for the study of structure but also have been in wide use as intermediates in organic synthesis are highly important from the industrial point of view, as well.

The dehydration-condensation reaction of sugars with ketones is known as the ketal formation reaction, and a variety of procedures have been known so far. With reference to the conventionally known procedures, use has been made of acid catalysts, such as mineral acids typified by sulfuric acid, hydrogen chloride, hydrogen bromide, phosphoric acid and perchloric acid, organic acids exemplified by acetic acid, trifluoroacetic acid, methanesulfonic acid, p-toluenesulfonic acid and acidic ion exchange resins, or Lewis acids exemplified by anhydrous aluminum chloride, tin tetrachloride, boron trifluoride, anhydrous zinc chloride and ferric chloride. Because this ketal formation reaction involves a dehydration-condensation reaction, it is common in almost all cases to use these acid catalysts in large quantities so that they may act as a dehydrating agent. When the used amounts of the acid catalysts are smaller, it is necessary to employ in large quantities of dehydrating agents which do not inhibit the reaction, such as phosphorus pentoxide, calcium chloride, anhydrous sodium sulfate, anhydrous copper sulfate, pyrosulfates, metaphosphoric acid esters, alum and molecular sieves.

As is described in the above, the conventional techniques require the utilization of a large amount of acid catalysts or dehydrating agents; this results in a complicated post-treatment of reaction products in the step of isolating the objective compound, and also allows used dehydrating agents and huge amounts of salts by-produced in the neutralization step to turn into industrial wastes. These techniques as an industrial production process, may be considered to involve a seriously controversial reaction, when judging from the viewpoints of post-treatment problems and saving of natural resources. In addition, it is one of the main defects of the conventional processes that side reactions such as self-condensation of ketones are ready to take place, because the catalysts to be employed in every case are strong acids.

The present inventor, after extensive investigation in order to overcome these defects of the conventional processes, discovered the entirely new finding that the reaction of sugar and ketone in the presence of antimony pentachloride or antimony pentafluoride can produce sugar ketals in improved yields, and the finding was followed by further research, which has culminated in the present invention.

The present invention is directed toward a process for producing a sugar ketal, which comprises reacting a sugar with a ketone in the presence of antimony pentachloride or antimony pentafluoride.

The sugars which can be used in the present invention are not specifically limited, and include for example tetroses such as erythrose, threose and erythrulose; pentoses such as arabinose, xylose, ribose, lyxose, rivulose and xylulose; hexoses such as glucose, galactose, talose, idose, gulose, mannose, altrose, fructose, sorbose, tagatose and psicose; sugar alcohols corresponding to sugars mentioned above such as erythritol, ribitol, arabitol, mannitol, sorbitol, dulcitol and innositol, and so forth; and deoxy-sugars such as rhamnose, fucose and 2-deoxyglucose and so on.

The ketones which are useful in the present invention are not specifically restricted, but specific examples thereof include an alkyl ketone having a carbon number of 3 to 7 such as acetone, methyl ethyl ketone, diethyl ketone, di-n-propyl ketone and di-i-propyl ketone; and a cyclic ketone having a carbon number of 5 to 7 such as cyclopentanone, cyclohexanone and cycloheptanone. The amount of these ketones to be used varies depending upon the structure of the objective compound, but such ketones are normally used at about 2 to 10 times the theoretical amount in number of moles, though they are preferably employed, for example, at not less than 1 mole per mole of a sugar, not less than 2 moles and not less than 3 moles per mole of a sugar in cases in which the objective compound is a monoketal, diketal and triketal, respectively. And, these ketones may be used as a reactant-solvent, whereby they may be employed in large excess, unless they exert any adverse effect on the reaction.

Antimony pentachloride or antimony pentafluoride which are usable in the present invention may be either in the form of anhydride or hydrate.

The amount of antimony pentachloride or antimony pentafluoride to be used is not less than about 0.01 weight % preferably in the range of catalytic amount (about 0.03 weight %) to about 10 weight %, more preferably in the range of about 0.05 weight % to about 5 weight %, all relative to the sugar. In addition, antimony pentachloride and antimony pentafluoride may be employed in combination.

As the reaction solvent, use can be made of any type of solvents, only if they do not interfere with the reaction. By way of example, there may be mentioned nitromethane, nitroethane, nitrobenzene, dichloromethane, chloroform, carbon tetrachloride, 1,1-dichloroethane, 1,2-dichloroethane, ethyl bromide, pentane, cyclopentane, hexane, cyclohexane, heptane, benzene, toluene and xylene, and furthermore, the above-mentioned ketones can be used both as reactant and solvent; the reaction can also be carried out in a mixed solvent consisting of not less than two kinds of these solvents. In order to increase the solubilities of sugars and catalysts in said solvent, a small amount of water may be added at the time of the initiation of reaction.

The present reaction is an equilibrium reaction, and because the removal of the water produced in the reaction generally improves the yields, the reaction may be carried out while eliminating the water from the reaction system by a known procedure. As the known procedure in such a case, there may be mentioned distillative removal of water or use of drying agents, and so forth. In the event of removing water by distillation, the technique utilizing azeotropy of solvent and water is generally employed; the water may be separated and removed from the liquid obtained by cooling the vapors produced by azeotropic distillation, whereby the remaining solvent may be returned to a reaction vessel, or the azeotropic vapors may be removed out of the reaction system, followed by a new addition of an equal amount of the dried solvent to the reaction system.

With reference to the procedure of using a drying agent, azeotropic vapors, directly or after being cooled to a liquid, may be dried with drying agents represented by anhydrous calcium sulfate, molecular sieves, alumina, etc. and subsequently returned to a reaction vessel.

The reaction temperature is normally in the range of about 0° C. to 150° C., preferably in the range of about 20° C. to 100° C. In order to adjust the azeotropic point of a mixture of the solvent or the ketone and water, the reaction may be conducted under reduced pressure.

The reaction time varies with the types of sugars and ketones, the amount of catalyst and reaction conditions, and is normally in the range of about 30 minutes to 10 hours, preferably in the range of about 1 hour to 8 hours.

In order to isolate the sugar ketal thus obtained from the reaction system, the reaction solvent may be distilled off as such, or after the reaction solution is adjusted to weakly alkaline pH (pH ca. 7 to 9) by the addition of a small amount of alkali (e.g., sodium bicarbonate, potassium bicarbonate, sodium carbonate, potassium carbonate, sodium hydroxide, potassium hydroxide, ammonia, pyridine, etc.) or an aqueous solution of said alkali. The objective sugar ketal can be easily obtained from the resulting residue by the known means, such as extraction, distillation, column chromatography or recrystallization.

The present invention provides an industrially favorable process for producing sugar ketals.

The process of the present invention, owing to the use in small amounts of antimony pentachloride or antimony pentafluoride which have been so far unknown as a catalyst for the acetal and ketal formation reaction, offers the characteristic features that the reaction can be allowed to proceed fully, that post-treatment of the reaction product is accordingly rendered outstandingly easy, with the objective sugar ketal being obtained in improved yields, that production of industrial wastes as is the case with the conventional processes is eliminated, that the utilization of catalyst in a small amount can reduce extremely the formation of byproducts (e.g., ketone dimer, etc.), shorten the reaction time and decrease a used amount of solvent, and so forth.

The examples are described below to illustrate the present invention more specifically.

EXAMPLE 1

To 200 ml of acetone were added 10.0 g of D-arabinose and 89.7 mg of antimony pentachloride, and the mixture was refluxed with stirring in a water bath of 60° C. for 8 hours. During this reaction, the refluxing solvent was dried with 20 g of Molecular Sieves 3A (synthetic zeolite produced by Wako Pure Chemical Industries, Ltd., Japan, average pore diameter : ca. 3Å) interposed between the reaction vessel and the condenser. After completion of the reaction, a small amount of pyridine was added to the reaction mixture, and the acetone was distilled off under reduced pressure. The residue was dissolved in benzene, and the solution was washed with aqueous sodium bicarbonate solution and water successively, and dried over anhydrous magnesium sulfate. After the solvent was distilled off under reduced pressure, the residue was distilled under reduced pressure to give 14.82 g (96.6%) of 1,2:3,4-di-O-isopropylidene-$\beta$-D-arabinopyranose (purity of not less than 99.8%) as a fraction having a boiling point of 84° C./2 mmHg. m.p. 39.5°–40.5° C.

Elemental analysis (%), for $C_{11}H_{18}O_5$: Calcd.: C, 57.38; H, 7.88. Found : C, 57.07; H, 7.81.

EXAMPLE 2

To 200 ml of acetone were added 10.0 g of D-arabinose and 43.3 mg of antimony pentafluoride, and the mixture was refluxed with stirring in a water bath of 60° C. for 7 hours. During this reaction, the refluxing solvent was dried with 20 g of Molecular Sieves 3A interposed between the reaction vessel and the condenser. After completion of the reaction, the total volume of the reaction solution was made up to 200 ml, and quantitative determination by gas chromatography [column: 3% Silicon OV-17 (Nishio Sangyo, Co. in Japan), on Uniport HPS(Gasukuro Kogyo Co.,Ltd. in Japan) 3 m, column temperature of 150° C.] showed that there was obtained 15.16 g (98.8%) of 1,2:3,4-di-O-isopropylidene-$\beta$-D-arabinopyranose.

EXAMPLE 3

To a mixed solution consisting of 100 ml of cyclohexanone and 100 ml of dichloromethane were added 10.0 g of D-arabinose and 89.7 mg of antimony pentachloride, and the mixture was refluxed with stirring in a water bath of 68° C. for 8 hours. During this reaction, the refluxing solvent was dried with 20 g of Molecular Sieves 3A interposed between the reaction vessel and the condenser. After completion of the reaction, a small amount of pyridine was added to the reaction solution, which was then diluted with benzene, washed with aqueous sodium bicarbonate solution and water successively and dried over anhydrous magnesium sulfate. The solvent and cyclohexanone, etc. were distilled off under reduced pressure to give 20.56 g (99.5%) of di-O-cyclohexylidene-D-arabinose (purity of not less than 98%) as a residue. m.p. 73.5°–75.5° C. (recrystallized from petroleum ether).

Elemental analysis (%), for $C_{17}H_{26}O_5$: Calcd.: C, 65.78; H, 8.44. Found : C, 65.70; H, 8.50.

EXAMPLE 4

To 200 ml of acetone were added 10.0 g of D-xylose and 89.7 mg of antimony pentachloride, and the mixture was refluxed with stirring in a water bath of 60° C. for 5 hours. During this reaction, the refluxing solvent was dried with 20 g of Molecular Sieves 3A interposed between the reaction vessel and the condenser. After completion of the reaction, a small amount of pyridine was added to the reaction solution, and the acetone was distilled off under reduced pressure. The residue was dissolved in benzene, and the benzene solution was washed with aqueous sodium bicarbonate solution and water successively, and dried over anhydrous magnesium sulfate. The benzene was distilled off under reduced pressure, and the resulting residue was distilled under reduced pressure to give 13.7 g (89.2%) of 1,2:3,5-di-O-isopropylidene-$\alpha$-D-xylofuranose as a fraction of 94 to 97° C./3 mmHg.

Elemental analysis (%), for $C_{11}H_{18}O_5$: Calcd.: C, 57.38; H, 7.88. Found : C, 57.40; H, 7.63.

EXAMPLE 5

To a mixed solution consisting of 100 ml of cyclohexanone and 100 ml of dichloromethane were added 10.0 g of D-xylose and 89.7 mg of antimony pentachloride, and the mixture was refluxed with stirring in a water bath of 68° C. for 8 hours. During this reaction, the refluxing solvent was dried with 20 g of Molecular Sieves 3A interposed between the reaction vessel and the condenser. The reaction solution was diluted with benzene, and was washed with aqueous sodium bicarbonate solution and water successively and dried over anhydrous magnesium sulfate. The solvent including cyclohexanone were distilled off under reduced pressure to give 17.4 g (84.2%) of 1,2:3,5-di-O-cyclohexylidene-α-D-xylofuranose (purity of not less than 98%) as a residue. The compound, when recrystallized from petroleum ether, showed m.p. of 104.5°–105.5° C.

Elemental analysis (%), for $C_{17}H_{26}O_5$: Calcd.: C, 65.78; H, 8.44. Found : C, 66.00; H, 8.62.

EXAMPLE 6

To a mixed solution consisting of 100 ml of cyclohexanone and 100 ml of dichloromethane were added 10.0 g of D-xylose and 65.0 mg of antimony pentafluoride, and the mixture was stirred in a water bath of 70° C. for 7 hours. During this reaction, the refluxing solvent was dried with 20 g of Molecular Sieves 3A interposed between the reaction vessel and the condenser. After completion of the reaction, the total volume of the reaction mixture was made up to 200 ml, and the quantitative analysis by gas chromatography (column: 3% Silicon OV-17, on Uniport HPS 3m, column temperature of 200° C.) showed that there was obtained 15.44 g (74.4%) of 1,2:3,5-di-O-cyclohexylidene-α-D-xylofuranose.

EXAMPLE 7

To 200 ml of acetone were added 10.0 g of D-glucose and 149.5 mg of antimony pentachloride, and the mixture was refluxed with stirring in a water bath of 60° C. for 8 hours. During this reaction, the refluxing solvent was dried with 20 g of Molecular Sieves 3A interposed between the reaction vessel and the condenser. After completion of the reaction, 1.60 g of the starting sugar was recovered by filtration. A small amount of pyridine was then added to the filtrate, and the acetone was distilled off under reduced pressure. The residue was dissolved in benzene, and the solution was washed with aqueous sodium bicarbonate and water, and dried over anhydrous magnesium sulfate. The benzene was distilled off under reduced pressure to give 10.46 g (72.4%) of 1,2:5,6-di-O-isopropylidene-α-D-glucofuranose. The compound, when recrystallized from a mixed solvent of chloroform-n-hexane (1:2), showed a melting point of 107°–109° C.

EXAMPLE 8

To a mixed solution consisting of 150 ml of cyclohexanone and 120 ml of dichloromethane were added 10.0 g of D-glucose and 299 mg of antimony pentachloride, and the mixture was refluxed with stirring in a water bath of 68° C. for 8 hours. During this reaction, the refluxing solvent was dried with 35 g of Molecular Sieves 3A interposed between the reaction vessel and the condenser. After completion of the reaction, 1.71 g of the starting sugar was recovered by filtration, and the reaction solution was diluted with chloroform, washed with aqueous sodium bicarbonate and water, and subsequently dried over anhydrous magnesium sulfate. The solvents including cyclohexanone were distilled off under reduced pressure, and the residue was recrystallized from ligroin to give 12.6 g (66.4%) of 1,2:5,6-di-O-cyclohexylidene-α-D-glucofuranose, m.p. 133°–136° C.

Elemental analysis (%), for $C_{18}H_{28}O_6$: Calcd.: C, 63.51; H, 8.29. Found : C, 63.40; H, 8.41.

EXAMPLE 9

To 200 ml of acetone were added 10.0 g of D-galactose and 89.7 mg of antimony pentachloride, and the mixture was refluxed with stirring in a water bath of 60° C. for 8 hours. During this reaction, the refluxing solvent was dried with 20 g of Molecular Sieves 3A interposed between the reaction vessel and the condenser. After completion of the reaction, a small amount of pyridine was added to the reaction mixture, and the acetone was distilled off under reduced pressure. The residue was dissolved in benzene, and the solution was washed with aqueous sodium bicarbonate and water, and dried over anhydrous magnesium sulfate. The benzene was distilled off, and the resulting residue was distilled under reduced pressure to give 11.97 g (82.9%) of 1,2:3,4-di-O-isopropylidene-α-D-galactopyranose as a fraction having a boiling point of 129°–133° C./0.2 mmHg.

Elemental analysis (%), for $C_{12}H_{20}C_6$: Calcd.: C, 55.37; H, 7.75. Found : C, 55.13; H, 7.66.

EXAMPLE 10

To 200 ml of acetone were added 10.0 g of D-mannose and 89.7 mg of antimony pentachloride, and the mixture was refluxed with stirring in a water bath of 60° C. for 8 hours. During this reaction, the refluxing solvent was dried with 20 g of Molecular Sieves 3A interposed between the reaction vessel and the condenser. After completion of the reaction, a small amount of pyridine was added to the reaction mixture, and the acetone was distilled off under reduced pressure. The residue was dissolved in benzene, and the solution was washed with aqueous sodium bicarbonate and water, and dried over anhydrous magnesium sulfate. The benzene was distilled off under reduced pressure to give 11.61 g (80.4%) of 2,3:5,6-di-O-isopropylidene-α-D-mannofuranose as a residue. The compound, when recrystallized from petroleum ether, showed m.p. 122°–123° C.

Elemental analysis (%), for $C_{12}H_{20}O_6$:
Calcd.: C, 55.37; H, 7.75.
Found : C, 55.35; H, 7.64.

EXAMPLE 11

To a mixed solution consisting of 100 ml of cyclohexanone and 100 ml of dichloromethane were added 10.0 g of D-mannose and 89.7 mg of antimony pentachloride, and the mixture was refluxed with stirring in a water bath of 68° C. for 8 hours. During this reaction, the refluxing solvent was dried with 20 g of Molecular Sieves 3A interposed between the reaction vessel and the condenser. The reaction mixture was diluted with benzene, washed with aqueous sodium bicarbonate and water, and dried over anhydrous magnesium sulfate. The solvents including cyclohexanone were distilled off under reduced pressure to give 16.49 g (87.3%) of 2,3:5,6-di-O-cyclohexylidene-α-D-mannofuranose as a residue. The compound, when recrystallized from cyclohexane, showed m.p. 122°–124° C.

Elemental analysis (%), for $C_{18}H_{28}O_6$: Calcd.: C, 63.51; H, 8.29. Found : C, 63.21; H, 8.18.

EXAMPLE 12

To 200 ml of acetone were added 10.0 g of D-fructose and 89.7 mg of antimony pentachloride, and the mixture was refluxed with stirring in a water bath of 60° C. for 8 hours. During this reaction, the refluxing solvent was dried with 20 g of Molecular Sieves 3A interposed between the reaction vessel and the condenser. After completion of the reaction, a small amount of pyridine was added to the reaction mixture, and the acetone was distilled off under reduced pressure. The residue was dissolved in benzene, and the benzene solution was washed with aqueous sodium bicarbonate and water successively, and then dried over anhydrous magnesium sulfate. The benzene was distilled off to give 12.09 g (83.7%) of 2,3:4,5-di-O-isopropylidene-β-D-fructopyranose. The compound, when recrystallized from n-hexane, showed m.p. 96°–98° C.

Elemental analysis (%), for $C_{12}H_{20}O_6$: Calcd.: C, 55.37; H, 7.75. Found : C, 55.30; H, 7.80.

EXAMPLE 13

To a mixed solution consisting of 150 ml of cyclohexanone and 150 ml of dichloromethane were added 20.0 g of D-fructose and 209.3 mg of antimony pentachloride, and the mixture was refluxed with stirring in a water bath of 68° C. for 8 hours. During this reaction, the refluxing solvent was dried with 35 g of Molecular Sieves 3A interposed between the reaction vessel and the condenser. After completion of the reaction, a small amount of pyridine was added to the reaction mixture, and the solvent was distilled off under reduced pressure. The residue was dissolved in benzene, and the benzene solution was washed with water, and dried ($Na_2SO_4$) and freed of the solvent under reduced pressure to get solidified. The solid material was recovered by filtration, washed with n-hexane containing a small amount of ether and dried to give 26.56 g (70.3%) of 2,3: 4,5-di-O-cyclohexylidene-β-D-fructopyranose. m.p. 142.5°–145° C. (recrystallized from n-hexane).

Elemental analysis (%), for $C_{18}H_{28}O_6$: Calcd.: C, 63.51; H, 8.29. Found : C, 63.89; H, 8.40.

EXAMPLE 14

To 200 ml of acetone were added 10.0 g of L-sorbose and 89.7 mg of antimony pentachloride, and the mixture was refluxed with stirring in a water bath of 61° C. for 8 hours. During this reaction, the refluxing solvent was dried with 35 g of Molecular Sieves 3A interposed between the reaction vessel and the condenser. After completion of the reaction, the total volume of the reaction mixture was adjusted to 200 ml, and the quantitative analysis by gas chromatography (column: 3% Silicon OV-17, on Uniport HPS 3m, column temperature; 160° C.) indicated that there was obtained 12.29 g (85.1%) of 2,3:4,6-di-O-isopropylidene-α-L-sorbofuranose.

EXAMPLE 15

To 200 ml of acetone were added 10.0 g of L-sorbose and 65.0 mg of antimony pentafluoride, and the mixture was refluxed with stirring in a water bath of 60° C. for 6 hours. During this reaction, the refluxing solvent was dried with 20 g of Molecular Sieves 3A interposed between the reaction vessel and the condenser. The quantitative analysis of the reaction solution according to the same procedure as described in Example 14 showed that there was obtained 11.89 g (82.3%) of 2,3:4,6-di-O-isopropylidene-α-L-sorbofuranose.

EXAMPLE 16

To a mixed solution consisting of 150 ml of cyclopentanone and 150 ml of dichloromethane were added 10.0 g of L-sorbose and 149.5 mg of antimony pentachloride, and the mixture was refluxed with stirring in a water bath of 65° C. for 8 hours. During this reaction, the refluxing solvent was dried with 20 g of Molecular Sieves 3A interposed between the reaction vessel and the condenser. After completion of the reaction, 3.5 g of the unreacted L-sorbose was filtered off, and the reaction solution was diluted with benzene, washed with aqueous sodium bicarbonate and water, and dried ($Na_2SO_4$). The solvents including cyclopentanone were distilled off under reduced pressure to give 9.07 g (80.5%, based on the consumed L-sorbose) of 2,3:4,6-di-O-cyclopentylidene-α-L-sorbofuranose. Melting point, 136°–138° C. (recrystallized from n-hexane)

Elemental analysis (%), for $C_{16}H_{24}O_6$: Calcd.: C, 61.52; H, 7.75. Found : C, 61.35; H, 7.80.

EXAMPLE 17

To 200 ml of acetone were added 10.0 g of L-rhamnose and 89.7 mg of antimony pentachloride, and the mixture was refluxed with stirring in a water bath of 60° C. for 8 hours. During this reaction, the refluxing solvent was dried with 20 g of Molecular Sieves 3A interposed between the reaction vessel and the condenser. After completion of the reaction, a small amount of pyridine was added to the reaction mixture, and the solvent was distilled off under reduced pressure. The residue was dissolved in benzene, and the benzene solution was washed with water, dried ($Na_2SO_4$) and freed of the solvent. The residue was purified by silica gel column chromatography to give 6.57 g (52.8%) of 2,3-O-isopropylidene-α-L-rhamnose. Melting point, 87°–88° C. (recrystallized from ether-petroleum ether).

Elemental analysis (%),for $C_9H_{16}O_5$: Calcd.: C, 52.93; H, 7.90. Found : C, 52.78; H, 7.99.

EXAMPLE 18

To a mixed solution consisting of 100 ml of diethyl ketone and 100 ml of dichloromethane were added 10.0 g of meso-erythritol and 21.3 mg of antimony pentafluoride, and the mixture was refluxed with stirring in a water bath of 65° C. for 7 hours. During this reaction, the refluxing solvent was dried with 20 g of Molecular Sieves 3A interposed between the reaction vessel and the condenser. After completion of the reaction, a small amount of pyridine was added to the reaction mixture, and the low-boiling substances were distilled off under reduced pressure. The residue was dissolved in benzene, and the benzene solution was washed with water, dried ($Na_2SO_4$) and freed of the solvent under reduced pressure, followed by distillation to give 20.62 g (97.5%) of 1,2:3,4-di-O-(3-pentilydene)-meso-erythritol (purity of not less than 99%). Boiling point, 118°–119° C./2.5 mmHg.

IR (neat) $cm^{-1}$: 1467, 1362, 1177, 1085, 9200

NMR ($CDCl_3$) δ: 0.87(t,12H), 1.41–1.78(m,8H), 3.8–4.15(m,6H)

EXAMPLE 19

To a mixed solution consisting of 100 ml of cyclohexanone and 100 ml of dichloromethane were added 10.0 g of meso-erythritol and 59.8 mg of antimony pentachloride, and the mixture was refluxed with stirring in a water bath of 68° C. for 8 hours. During this reaction, the refluxing solvent was dried with 20 g of Molecular Sieves 3A interposed between the reaction vessel and the condenser. After completion of the reaction, a small amount of pyridine was added to the reaction solution, and the solvent was distilled off under reduced pressure.

The residue was dissolved in benzene, and the benzene solution was washed with water, dried (Na$_2$SO$_4$) and freed of the solvent under reduced pressure to give 22.31 g (96.5%) of 1,2:3,4-di-O-cyclohexylidene-meso-erythritol (purity of not less than 98%). Melting point, 95°–96° C.

NMR (CDCl$_3$)δ: 1.2–1.8 (broad, 20H), 3.8–4.2(m, 6H)

EXAMPLE 20

To 200 ml of acetone were added 10.0 g of D-mannitol and 65 mg of antimony pentafluoride, and the mixture was refluxed with stirring in a water bath of 60° C. for 7 hours. During this reaction, the refluxing solvent was dried with 20 g of Molecular Sieves 3A interposed between the reaction vessel and the condenser. After completion of the reaction, a small amount of pyridine was added to the reaction solution, and the solvent was distilled off under reduced pressure. The residue was dissolved in chloroform, and the solution was washed with aqueous sodium bicarbonate and water, and dried over anhydrous magnesium sulfate. The solvent was distilled off under reduced pressure to give 17.43 g (93.3%) of 1,2:3,4:5,6-tri-O-isopropylidene-D-mannitol. Melting point, 68.5°–70.5° C. (recrystallized from 70% ethanol).

Elemental analysis (%), for C$_{15}$H$_{26}$O$_6$: Calcd.: C, 59.58; H, 8.67. Found : C, 59.60; H, 8.80.

EXAMPLE 21

To a mixed solution consisting of 150 ml of cyclohexanone and 150 ml of dichloromethane were added 10.0 g of D-mannitol and 209.3 mg of antimony pentachloride, and the mixture was refluxed with stirring in a water bath of 68° C. for 8 hours. During this reaction, the refluxing solvent was dried with 20 g of Molecular Sieves 3A interposed between the reaction vessel and the condenser. After completion of the reaction, a small amount of pyridine was added to the reaction mixture, and the solvent was distilled off under reduced pressure. The residue was dissolved in benzene, and the benzene solution was washed with water, dried (Na$_2$SO$_4$) and freed of the solvent under reduced pressure. The resulting oily material, upon standing at room temperature, solidified. The solid was recovered by filtration, washed with a small amount of hexane and dried to give 22.85 g (98.4%) of 1,2:3,4:5,6-tri-O-cyclohexylidene-D-mannitol. Melting point, 84° C. (recrystallized from n-hexane)

Elemental analysis (%), for C$_{24}$H$_{38}$O$_6$L Calcd.: C, 68.22; H, 9.06. Found : C, 68.57; H, 8.86.

EXAMPLE 22

To 200 ml of acetone were added 10.0 g of D-glucose and 86.7 mg of antimony pentafluoride, and the mixture was refluxed with stirring in a water bath of 60° C. for 7 hours. During this reaction, the refluxing solvent was dried with 20 g of Molecular Sieves 3A interposed between the reaction vessel and the condenser. After completion of the reaction, 1.30 g of the unreacted D-glucose was filtered off, and the total volume of the reaction solution was made up to 200 ml, and the quantitative analysis by gas chromatography (column: 3% Silicon OV-17, on Uniport HPS 3m, temperature of column: 170° C.) indicated that there was obtained 12.13 g (84.0%) (96.5%, based on the consumed D-glucose) of 1,2: 5,6-di-O-isopropylidene-α-D-glucofuranose.

What I claim is:

1. A process for producing a sugar ketal, which comprises reacting a tetrose, a pentose, a hexose, or a sugar alcohol or a deoxy-sugar thereof with a ketone in the presence of antimony pentachloride or antimony pentafluoride.

2. The process according to claim 1, wherein the pentose is arabinose or xylose.

3. The process according to claim 1, wherein the hexose is sorbose, glucose, mannose, fructose or galactose.

4. The process according to claim 1, wherein the sugar alcohol is erythritol or mannitol.

5. The process according to claim 1, wherein the deoxysugar is rhamnose.

6. The process according to claim 1, wherein the ketone is an alkyl ketone having a carbon number of 3 to 7 or a cyclic ketone having a carbon number of 5 to 7.

7. The process according to claim 6, wherein the alkyl ketone is acetone or diethyl ketone.

8. The process according to claim 6, wherein the cyclic ketone is cyclohexanone or cyclopentanone.

* * * * *